United States Patent [19]

Hitzman et al.

[11] Patent Number: 4,556,635
[45] Date of Patent: Dec. 3, 1985

[54] DETERMINATION OF ALCOHOL CONTENT IN WATER IMISCIBLE ORGANIC SYSTEMS

[75] Inventors: Donald O. Hitzman; Thomas R. Hopkins, both of Bartlesville, Okla.

[73] Assignee: Phillips Petroleum Company, Bartlesville, Okla.

[21] Appl. No.: 527,540

[22] Filed: Aug. 29, 1983

[51] Int. Cl.$^4$ ............... C12Q 1/26; C12N 11/02; C12R 1/84
[52] U.S. Cl. .......................... 435/25; 204/403; 435/177; 435/178; 435/179; 435/180; 435/182; 435/817; 435/938; 436/131; 436/132
[58] Field of Search .............. 435/25, 176, 177, 178, 435/179, 180, 182, 817, 938; 436/131, 132; 204/403

[56] References Cited

U.S. PATENT DOCUMENTS 4,073,713  2/1978  Newman .................. 435/181 X
4,119,494 10/1978  Durand et al. ................ 435/176

FOREIGN PATENT DOCUMENTS 1507810  4/1978  United Kingdom .

OTHER PUBLICATIONS

Butler, "Enzymes in Non-Aqueous Solvents", *Enzyme Microb. Technol.*, 1, pp. 253–259, (1979).
Guilbault et al., "Amperometric Enzyme Electrodes Part III, Alcohol Oxidase", *Analytica Chemica Acta*, 69, pp. 189–194, (1974).
Klibanov et al., "A New Approach to Preparative Enzymatic Synthesis", *Biotechnology and Bioengineering*, XIX pp. 1351–1361, (1977).
Clark, Jr., *Biotechnol. & Bioeng.* Symp. No. 3, 1972, pp. 377–394, (John Wiley & Sons, Inc.).
Couderc, et. al., *Agric. Biol. Chem.* vol. 44, No. 10, 1980, pp. 2279–2289.

*Primary Examiner*—David M. Naff

[57] ABSTRACT

The concentration of a $C_1$ to $C_4$ alcohol in an essentially water immiscible organic system is accurately determined by a simple and quick process. A sample of the water immiscible organic system containing less than about 0.01% (W/V) of the alcohol is contacted with an aqueous layer of alcohol oxidase immobilized on an electrode for measuring dissolved oxygen content. Ethanol in the water immiscible organic system partitions into the aqueous layer where alcohol oxidase catalyzes oxidation of the alcohol. Oxygen consumed during the oxidation is measured by the electrode, and the concentration of alcohol determined therefrom. To obtain less than about 0.01% alcohol in the sample, the sample may be diluted with the water immiscible organic system.

7 Claims, No Drawings

DETERMINATION OF ALCOHOL CONTENT IN WATER IMISCIBLE ORGANIC SYSTEMS

This invention relates to a process for the determination of alcohol concentration in water immiscible organic systems.

The use of alcohol oxidase test probes to determine lower chain alcohol concentration is known to those skilled in the art. Such enzyme probes are useful for measuring the alcohol levels in biological fluids, for example blood, and the like. The ability of such enzyme probes to measure alcohol content in organic systems, though, has been severely limited because enzyme structure is altered in substantially non-aqueous systems and hence are unable to display their characteristic catalytic activity.

Currently, a simple and quick yet accurate method for determining the alcohol content in organic systems is needed. Such an analytical process would be particularly desirable for measuring the alcohol content of gasohol (i.e. a blend of gasoline and ethyl alcohol).

Therefore it is an object of this invention to provide an analytically accurate method for determining the amount of alcohol present in a water immiscible organic system.

Other aspects, objects, and the several advantages of the present invention are apparent from the specification and appended claims.

In accordance with the present invention, we have discovered that the alcohol content of an essentially water immiscible organic system may be accurately determined in a simple and quick process which comprises contacting a sample of the organic system containing less than about 0.01% (w/v) of said alcohol with an enzyme probe consisting of a dissolved oxygen electrode having alcohol oxidase immobilized thereon and thereafter measuring the change in oxygen concentration in the immobilized alcohol oxidase enzyme layer.

In the present invention, alcohols contemplated for measurement are straight chain $C_1$ to $C_4$ alcohols, most typically methanol and ethanol.

For the purposes of this invention, the term essentially water immiscible organic system is defined to be any liquid organic substance which has a solubility of less than about 5% (w/v) in water. Examples of such essentially water immiscible systems include chloroform, ether, alcohol esters of aliphatic acids, hydrocarbons, etc. A typical essentially water immiscible organic substance which can contain alcohol is gasoline as mentioned earlier. Gasoline is typically a refined petroleum naphtha obtained by such processes as the distillation of crude oil and the stripping or condensation of natural gas.

In this invention, any alcohol oxidase known in the art or available from commercial supply houses such as Sigma Chemical Company, St. Louis, Mo. may be used.

Alternatively, alcohol oxidase can be prepared from an aqueous suspension of *Pichia pastoris*. In preparing the enzyme, an aqueous fluid containing a suspension of cells is homogenized to produce a homogenate. Suspended solids are removed from the homogenate to produce a crude solution containing soluble alcohol oxidase. The crystalline form of the enzyme can be obtained by methods of ultra filtration, and preferably by dialysis. Dialysis involves dialyzing the crude solution, prepared by homogenizing an aqueous fluid having a cell density effective for crystallization of alcohol oxidase in a recovery range solution having a molar ionic strength in the range of between 0.05M and about 0.01M, against a dialysis medium across a membrane impermeable to the alcohol oxidase but permeable to dialysis medium water and buffer molecules, if any, to achieve on the enzyme side of the membrane the recovery range solution thereby resulting in crystalline alcohol oxidase, and separating the resulting crystalline alcohol oxidase from the dialysis medium. Such an enzyme isolation procedure is shown in Example I.

The enzyme thus prepared is characterized by the following properties. It has 8 subunits of an estimated molecular weight of 78,000 per subunit as determined by SDS gel electrophoresis. The enzyme is a flavoprotein having FAD (flavin adenine dinucleotide) coenzyme. The apparent Michaelis constant (Km) for methanol is about 0.7. The enzyme is further characterized by its reaction with various alcohols.

The alcohol oxidase of this invention catalyzes the following reaction $$RCH_2OH + O_2 \rightarrow RCHO + H_2O_2$$

where R is hydrogen or lower alkyl, generally selected from the group consisting of H—, $CH_3$—, $CH_3CH_2$—, and $CH_3(CH_2)_2$—. 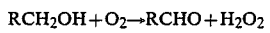 Other alcohols catalyzed by yeast alcohol oxidase include propargyl alcohol, allyl alcohol, mercapto ethanol, and the hydrated form of formaldehyde.

Since in the course of the reaction oxygen is consumed and aldehydes and hydrogen peroxide are produced, alcohol oxidase can be used to determine the concentrations of short chain alcohols, $RCH_2OH$, in a fluid sample under conditions compatible with enzymatic activity. More specifically, alcohol oxidase can be used to determine the concentration of lower alcohols such as methanol or ethanol in gasohol.

A particularly convenient way of determining such alcohol concentrations by enzymatic methods is by immobilizing the alcohol oxidase on the tip of a dissolved oxygen electrode. In such a configuration the assay method can be considered reagentless, as the enzyme electrode can be reused numerous times without any added chemical reagents. Several such polarographic dissolved oxygen electrodes are commercially available and are suitable for utilization with alcohol oxidase enzyme. For example, a Clark dissolved oxygen electrode can be used. Other DO probes based on a galvanic (fuel cell) principles can be used. In addition, one product of the alcohol oxidase catalyzed oxidation of alcohols is $H_2O_2$ electrochemical probe having immobilized alcohol oxidase on its sensor area.

The alcohol oxidase can be immobilized on the electrode tip by any suitable method. For example, the enzyme can be blended with suitable supporting materials to form a paste which is held as a thin film on the electrode tip by a membrane permeable (typically hydrated) to the compound whose concentration is to be determined, but impermeable to the enzyme itself. For example, the supporting material may be hydrated DEAE Sephadex, a polysaccharide ion exchange resin from Pharmacia Fine Chemicals, Sweden. For ethanol determinations, a suitable membrane is cellulose acetate film through which film ethanol has a satisfactory mobility. Of course, the enzyme can also be covalently bonded to an appropriate electrode membrane or can be physically incorporated in an appropriate polymer film. However the enzyme is immobilized, it must be present in an aqueous environment such that the alcohol in the water immiscible organic solvent can partition into the aqueous, enzyme phase and enter into catalytic oxidation of the alcohol substrate. The hydrated environment is typically provided by either a hydrated outer membrane such as cellulose acetate or a hydrated immobilization agent such as hydrated DEAE Sephadex.

Conditions compatible with enzymatic activity include a fluid containing less than about 0.01% (w/v) of said alcohol and a fluid sample temperature in the range of about 25° C. up to and including 45° C. and preferably at about 25° C. for convenience.

Several 10x dilutions with the appropriate water immiscible organic system may be necessary to get the alcohol concentration in the system less than about 0.01% (w/v). For example, in the case of gasohol (typically about 10% (w/v) ethanol) at least three 10x dilutions with gasoline would be necessary to bring the concentration of the ethanol down to less than 0.01% (w/v). The 0.01% (w/v) concentration level is a practical rather than an arbitrary limitation because for values of measured substance (alcohol) above the 0.01% (w/v) level the alcohol oxidase probe may be too sensitive to use as an accurate analytical device.

Preferably, a calibration curve is prepared using a series of known concentrations of the alcohol to be assayed. To determine the alcohol concentration, the sample electrode is immersed in a thus prepared fluid (i.e. alcohol in water immiscible organic solvent) to be examined. The substrate alcohol diffuses across the membrane and in the presence of oxygen reacts to produce an aldehyde product and hydrogen peroxide. The reaction is monitored by observing the absolute change or rate of change of oxygen concentration in the enzyme layer. Since the catalyzed reaction is stoichiometric, the concentration of the alcohol, $RCH_2OH$, can be determined from the absolute change or rate of change in oxygen concentration by techniques known to those skilled in the art.

The following examples further illustrate the present invention.

Example I

In a continuous aerobic fermentation process, methanol and an aqueous mineral salts medium in a volume ratio of about 40 to 60, respectively, were fed individually to a fermenter, inoculated with the yeast species *Pichia pastoris* NRRL Y-11430, at a rate so that methanol is the growth-limiting factor. The fermenter was a 1500-liter foam-filled fermenter with a liquid volume of about 610 liters, with automatic pH, temperature, and level control. Agitation was provided by two conventional paddle-type turbines driven at 1000 rpm. The aeration rate was about 4 volumes of air (at about 38 psig and about 25° C.) per volume of ferment in the fermenter per minute. Anhydrous ammonia was added at such a rate as to maintain the pH of the fermentation mixture at about 3.5.

The aqueous mineral salts medium was prepared by mixing, with each liter of tap water, 15.86 mL 75 percent $H_3PO_4$, 9.53 g $K_2SO_4$, 7.8 g $MgSO_4.7H_2O$, 0.6 g $CaCl_2.2H_2O$, and 2.6 g 85 percent KOH. The trace mineral solution plus biotin was fed separately via the methanol stream at a rate of 10 mL per liter of methanol. The trace mineral solution plus biotin was prepared by mixing 780 mL of a trace mineral solution, 20 mL water, 200 mL methanol and 0.032 g biotin.

The trace mineral solution was prepared by mixing, for each liter of solution, 65 g $FeSO_4.7H_2O$, 20 g $ZnSO_4.7H_2O$, 3.0 g $MnSO_4.H_2O$, 6.0 g $CuSO_4.5H_2O$, 5.0 mL conc. $H_2SO_4$, and sufficient deionized water to make 1 liter of solution.

The aqueous mineral salts medium was fed at a rate of b 3.15 liters per hour and the methanol at a rate of 21 liters per hour.

The fermentation was conducted at about 30° C. and about 38 psig pressure, with a retention time of 11.6 hours.

Fermentation of *Pichia pastoris* NRRL Y-11430 was carried out by a method of which that set forth above is typical. A portion of the fermenter effluent was removed and adjusted to pH 7.5 with ammonium hydroxide, and was homogenized on a Dyno-Mill ® Model KDL using a 0.6 liter vessel in a continuous operation at 30° C. using belt combination #3 and a flow of 20–30 mL/hr. The beads in the mill were lead-free glass beads with a diameter of 0.3–0.5 mm. The resulting homogenate was centrifuged at 5° C. and 20,000 x g for 30 minutes to yield a cell-free supernatant. The cell-free supernatant enzyme activity measured by dye-peroxidase method described below was about 330 EU/mL. This describes the preparation of crude yeast homogenate.

Six 130 mL portions of the supernatant were placed in cellulose acetate dialysis bags and dialyzed at 5° C. against about 8 liters of distilled water. After 4 days, the aqueous phase of each bag was decanted. The solids remaining in the bags consisted of two types of solid. The thin upper white layer was carefully removed and discarded. The bottom solid was brown-yellow and was crystalline alcohol oxidase. A portion of the crystalline alcohol oxidase was dissolved in distilled water (about 10 times the volume of the solid) and an assay by the dye-peroxidase method described below showed an activity of 94 EU/mL. The specific activity of the alcohol oxidase was 10.4 EU/mg of protein.

A sample of the solid alcohol oxidase was examined by SDS gel electrophoresis and a single band was observed indicating a homogeneously pure enzyme. A comparison of electrophoretic mobility with those of proteins having known molecular weight indicates a subunit molecular weight of about 72,000±3000 (estimated). This describes the preparation of pure yeast alcohol oxidase from *Pichia pastoris*.

EXAMPLE II

CONSTRUCTION OF ALCOHOL OXIDASE/DISSOLVED OXYGEN PROBE

The alcohol oxidase isolated from *Pichia pastoris* was immobilized on the tip of a dissolved oxygen electrode (Beckman Model 777) as follows: A concentrated solution of alcohol oxidase (~100 mg/mL) in water and hydrated DEAE Sephadex (in weight ratio of about 1:1) were mixed and applied to the Teflon membrane on the tip of the Beckman dissolved oxygen probe. A cellulose acetate dialysis membrane with molecular weight cut-off of 12,000–14,000 was used to hold the alcohol oxidase-DEAE Sephadex mixture to the electrode tip. The electrode circuitry was attached to an analog differentiator which gave the analysis results as a peak height which is proportional to the rate of dissolved oxygen removal from the reaction mixture held between the Teflon and cellulose acetate dialysis membranes. The initial rate of dissolved oxygen removal is directly proportional to the amount of alcohol in the sample.

The electrode was calibrated with a series of standard ethanol solutions. In each case, the sample was added to the bulk solution in the electrode chamber which contained 3.3 mL of aerated 0.05M potassium phosphate buffer (pH 7.5) at 25° C. The calibration curve of peak height vs. alcohol concentration was linear up to a final concentration in the bulk solution of about 0.001 volume % alcohol (10 ppm). The electrode exhibited rapid response (assay time of about 15 seconds) and was sensitive to concentration of ethanol as low as 0.2 ppm by volume.

EXAMPLE III

DYE-PEROXIDASE ASSAY

Alcohol oxidase activity was determined using a leuco dye and peroxidase to quantitate the amount of $H_2O_2$ produced. A dye-buffer mixture was prepared by mixing 0.1 mL of an o-dianisidine solution (1 weight percent o-dianisdine in water) with 12 mL of aerated 0.1M sodium phosphate buffer (pH 7.5). The assay mixture was prepared with 2.5 mL of the dye-buffer mixture, 50 μL of methanol, 10 μL of a peroxidase solution (1 mg of horse-radish peroxidase-Sigma, Type II), and 25 μL of the alcohol oxidase solution. The assay mixture was maintained at 25° C. in a 4×1×1 cm cuvette and the increase in absorbance by the dye at 460 nm was recorded for 2 to 4 minutes. The enzyme activity was calculated by $$\text{Activity } (\mu \text{ mole/min/mL or Enzyme Units/mL}) = \frac{\Delta A}{\text{min.}} \times 11.5$$

wherein 11.5 is a factor based on a standard curve prepared with known aliquots of $H_2O_2$ and $\Delta A$ is the change in absorbance during the experimental interval.

EXAMPLE IV

STABILITY OF ALCOHOL OXIDASE IN THE PRESENCE OF GASOLINE

A saturated solution of alcohol oxidase (~100 mg/mL) in water was diluted with a ten-fold volume of water. The resulting solution containing ~10 mg/mL alcohol oxidase was mixed with an aliquot of gasoline of sufficient amount to saturate the aqueous phase with the hydrocarbon and incubated at room temperature for a period of time to determine enzyme stability. Thus, 0.5 mL of alcohol oxidase containing solution was assayed for enzyme activity, then 2 μL of gasoline added, and the sample assayed for alcohol oxidase activity over several hours.

| Time | EU/mL* |
|---|---|
| 0 | 128 |
| 5 min | 125 |
| 10 min | 140 |
| 30 min | 133 |
| 1 hr | 151 |
| 2 hr | 140 |
| 3 hr | 129 |
| 4 hr | 129 |

*measured by dye-peroxidase method described above.

The result of this example demonstrate that prolonged exposure of the enzyme alcohol oxidase to relatively low concentrations of hydrophobic hydrocarbons such as gasoline does not significantly affect enzyme activity.

EXAMPLE V

A galvanic dissolved oxygen probe was constructed using a silver wire as the anode and aluminum as the cathode. The tip of the anode was covered with a fluorocarbon membrane, then a layer of alcohol oxidase in DEAE-Sephadex gel and finally a layer of cellulose acetate membrane as described in Example II.

The probe was then placed in 40 ml of a stirred solvent consisting of either water or cyclohexane contained in a small open beaker. Aliquots of 0.1% (v/v) or 1.0% (v/v) ethanol were added to the solvent and the relative decrease in the dissolved oxygen signal (ΔH) was recorded, the results being listed below.

| Run | | ΔH |
|---|---|---|
| | Added 1.0% ethanol in water solvent, μL | |
| 1 | 10 | 1.6 |
| 2 | 50 | 8.7 |
| 3 | 100 | 17.4 |
| | Added 0.1% ethanol in cyclohexane, μL | |
| 4 | 10 | 7 |
| 5 | 20 | 12 |
| 6 | 30 | 15 |

The above runs (4–6) demonstrate that not only is the enzyme-electrode probe operable for measuring ethanol concentration in a water immiscible organic system such as cyclohexane, but also the probe sensitivity to ethanol is increased about 30 fold over that measured with the water solvent (Runs 1–3).

Reasonable modifications and variations are possible from the foregoing without departing from the spirit and scope of the present invention.

We claim:

1. A process for the determination of the concentration of a $C_1$ to $C_4$ alcohol in an essentially water immiscible organic system having a solubility of less than about 5% (w/v) in water comprising the steps of:
   (a) contacting a sample of the essentially water immiscible organic system containing less than about 0.01% (w/v) of said alcohol with alcohol oxidase immobilized on an electrode having a sensing area for measuring dissolved oxygen content, said alcohol oxidase being immobilized on the electrode with a hydratd support material layer bound to the sensing area of the electrode, said hydrated support material layer providing an aqueous phase containing the alcohol oxidase such that the alcohol in said water immiscible organic system can partition into the aqueous phase and be oxidized by oxygen in the aqueous phase, catalyzed by said alcohol oxidase; and
   (b) thereafter determining the alcohol concentration in said essentially water immiscible organic system by measuring with said electrode the oxygen consumed by the oxidation of the alcohol partitioned into the aqueous phase, catalyzed by said alcohol oxidase.

2. A process according to claim 1 wherein said alcohol is methanol.

3. A process according to claim 1 wherein said alcohol is ethanol.

4. A process according to claim 1 wherein said water immiscible organic system is cyclohexane.

5. A process according to claim 1 wherein said water immiscible organic system is gasoline.

6. A process according to claim 1 wherein said alcohol oxidase is derived from Pichia pastoris.

7. A process according to claim 1 wherein said alcohol is ethanol and said water immiscible organic system is cyclohexane.

* * * * *